(12) United States Patent
Mock et al.

(10) Patent No.: US 8,333,688 B2
(45) Date of Patent: Dec. 18, 2012

(54) RECOVERABLE INTRA-UTERINE SYSTEM

(75) Inventors: Pascal Mock, Genève (CH); Nicolas Bouche, Les Paccots (CH); Philippe Le Goff, Chemin de la Biolleyre (CH)

(73) Assignee: Anecova SA, Lausanne (CH)

( * ) Notice: Subject to any disclaimer, the term of this patent is extended or adjusted under 35 U.S.C. 154(b) by 814 days.

(21) Appl. No.: 12/374,290

(22) PCT Filed: Jun. 26, 2007

(86) PCT No.: PCT/IB2007/002913
§ 371 (c)(1),
(2), (4) Date: Jan. 16, 2009

(87) PCT Pub. No.: WO2008/012685
PCT Pub. Date: Jan. 31, 2008

(65) Prior Publication Data
US 2009/0299129 A1    Dec. 3, 2009

(30) Foreign Application Priority Data
Jul. 21, 2006 (FR) ..................................... 06 53069

(51) Int. Cl.
*A61B 17/43* (2006.01)
*A61F 6/06* (2006.01)
*A61F 6/14* (2006.01)
(52) U.S. Cl. ........... 600/34; 128/833; 128/839; 128/840
(58) Field of Classification Search ............... 600/33–35; 128/830–840
See application file for complete search history.

(56) References Cited

U.S. PATENT DOCUMENTS

| 3,410,265 | A | * | 11/1968 | Chaft | 128/839 |
| 3,467,089 | A | * | 9/1969 | Hasson | 128/839 |
| 3,656,483 | A | | 4/1972 | Rudel | |
| 3,716,052 | A | * | 2/1973 | Chaft | 128/839 |
| 3,845,761 | A | * | 11/1974 | Zaffaroni | 128/833 |
| 4,312,347 | A | | 1/1982 | Magoon et al. | |
| 2004/0261799 | A1 | * | 12/2004 | Mock | 128/833 |

FOREIGN PATENT DOCUMENTS
EP    1 639 972 A1    3/2006
WO    03/011200       2/2003

* cited by examiner

*Primary Examiner* — Kevin C Sirmons
*Assistant Examiner* — Ophelia A Hawthorne
(74) *Attorney, Agent, or Firm* — Hunton & Williams, LLP

(57) ABSTRACT

The recoverable intra-uterine system comprises a housing capable of containing one or a plurality of elements selected from among the group comprising an embryo, male and/or female gametes, a fertilized oocyte, and unfertilized ovum and a combination of these elements, the housing having along an axis a distal end and a proximal end, and a device for holding the recoverable intra-uterine device in the uterus. The holding device is arranged at the proximal end of the housing and includes at least one holding arm in the uterine cavity capable of taking at least two positions: —one free position in which at least one holding arm is separated from the axis; and —a retracted position in which at least one holding arm is substantially parallel to the axis. Use in medically assisted reproduction techniques.

10 Claims, 5 Drawing Sheets

RECOVERABLE INTRA-UTERINE SYSTEM

CROSS-REFERENCE TO RELATED APPLICATIONS

This application is the U.S. National Phase Application of International Application No. PCT/IB2007/002913, filed Jun. 26, 2007, which claims the benefit of French Application No. FR 0653069, filed Jul. 21, 2006, the disclosures of each of which is hereby incorporated by reference.

FIELD OF THE INVENTION

The present invention concerns a recoverable intra-uterine system.

It is generally concerned with stabilizing and retaining in position a recoverable intra-uterine system used in the process of medically assisted procreation.

BACKGROUND

Intra-uterine systems that can be implanted and recovered non-invasively have been known for a number of years.

Generally speaking, these systems can be classified into three major families according to their indication or their mode of action. Of these, devices having an anti-conception indication, such as contraceptive IUDs, represent the great majority of cases and constitute the first category.

The second category consists of capsules loaded with a therapeutic substance and placed in the uterine cavity for diffusion and action in the organism.

Finally, the third category consists of intra-uterine devices indicated for in vivo assistance in medically assisted procreation processes. Thus there is known an intra-uterine device as notably described in the document WO 03/011200, intended to be placed in the uterine cavity for a period between a few hours and a few days, and enabling pre-implantation development of an embryo in vivo.

For each of these categories of devices, it is of primordial importance that the object placed in the uterine cavity non-invasively can remain positioned at the determined location for the indicated period and then recovered non-invasively.

To meet these specifications, the devices concerned must address two constraints, a priori contradictory. On the one hand, these devices must be both thin and compact to be placed in the uterine cavity and then removed, non-invasively, which imposes the passing through the cervical channel of the cervix. Moreover, they must be sufficiently bulky to be stabilized in the uterine cavity and not to be expelled by the natural contractions of the uterus.

In the prior art numerous variants and shapes have been proposed to address this two-fold constraint, but oriented exclusively to applications belonging to the first and second categories of devices described above.

Now, for the third category of devices used in the process of medically assisted procreation in vivo, an additional constraint becomes apparent when it is of primordial importance to preserve the integrity of the endometrium. This is because implantation of the embryo must take place in the same menstrual cycle of the patient and the endometrium must not be damaged in any way prior to implanting the embryo.

In particular, existing stabilization systems in the field of contraception, and in particular for retaining a contraceptive IUD in position in the uterus, are not satisfactory. This is because they can damage the endometrium, not only when retaining the device in position in the uterine cavity, by exerting a constant pressure against the endometrium (causing phenomena of contractions, possibly with hormonal activation), but also during removal of the device, the retaining elements rubbing on the endometrium over a great distance, thereby causing microlesions or inflammatory inductions, or bleeding.

Also, the document WO 03/011200 describes an intra-uterine device carrying stabilizing fins at a distal end of the housing. These stabilizing fins are liable to damage the endometrium, notably during removal of the device, and thereby to reduce the chances of successful subsequent implantation of the embryo.

SUMMARY OF THE INVENTION

An object of the present invention is to propose a recoverable intra-uterine system that removes the drawbacks cited above and in particular guarantees that the system is held in position in the uterine cavity and preserves the integrity of the endometrium, notably during removal of the system.

To this end, the present invention concerns a recoverable intra-uterine system comprising a housing adapted to contain one or a plurality of elements selected from among the group comprising an embryo, male and/or female gametes, a fertilized ovocyte, an unfertilized ovum and a combination of these elements, the housing having along an axis a distal end and a proximal end, and a device for retaining the recoverable intra-uterine device in the uterus.

According to the invention, the retaining device is arranged at the proximal end of the housing and includes at least one retaining arm in the uterine cavity adapted to assume at least two positions:

a free position in which said at least one retaining arm is away from said axis; and a removal position in which said at least one retaining arm is substantially parallel to said axis.

Accordingly, thanks to the arrangement of the retaining device at the proximal end of the housing, the system introduced into the uterus is held in position in the region of the cervical channel and the area of contact between the retaining arm or arms of the retaining device and the endometrium is small. The beneficial effects of these features reduce the pressure induced by the intra-uterine system on the uterine cavity.

Moreover, during removal of the device, the retaining arm lying substantially on the axis of the housing, there is very limited or even no rubbing on the wall of the endometrium beyond the cervical channel.

Furthermore, thanks to the arrangement of the retaining device in the uterine cavity at the proximal end of the housing, the active part of the system, consisting of the housing, is positioned above the retaining arm or arms in the uterine cavity, and thus entirely enclosed within the uterine cavity.

Moreover, when the system is placed in the uterine cavity with its associated retaining device, the retaining arm(s) is or are inside the uterine cavity, beyond the cervix, and are not liable to obstruct the cervix and to impede the existing flow of fluid between the uterus and the vagina.

According to one particular feature of the invention, said at least one retaining arm is further adapted to assume an introduction position in which said at least one retaining arm is substantially parallel to said axis and is an extension of housing.

Thanks to this particular arrangement of the retaining device, the retaining arm being aligned with the housing, the whole of the system can be introduced into a standard transfer catheter used to introduce the recoverable intra-uterine system into the uterine cavity beyond the cervix.

When the arm is aligned with the housing, the retaining device does not form any increased thickness around the housing and can be introduced into a transfer catheter with a small inside diameter, and thus a small outside diameter, adapted to pass through the cervix.

According to an advantageous feature of the invention, said at least one retaining arm is arranged on elastic means exerting a return force adapted to retain said at least one retaining arm in the free retaining position.

Thanks to the presence of these elastic means, the arm(s) of the retaining device is or are automatically placed in their free retaining position when the recoverable intra-uterine system is introduced into the uterine cavity, after removal of the transfer catheter used to introduce it.

The recoverable intra-uterine system is therefore held in position in a reliable and natural manner without requiring additional manipulation by the practitioner.

Another aspect of the invention is directed to a combination of a transfer catheter and an intra-uterine system wherein said system is housed in the catheter.

The housing and the associated retaining device can therefore be placed in the uterus using the transfer catheter.

Other features and advantages of the invention will become more apparent in the following description.

BRIEF DESCRIPTION OF THE DRAWINGS

In the appended drawings, provided by way of nonlimiting example.

DETAILED DESCRIPTION OF PREFERRED EMBODIMENTS

Figure 1:
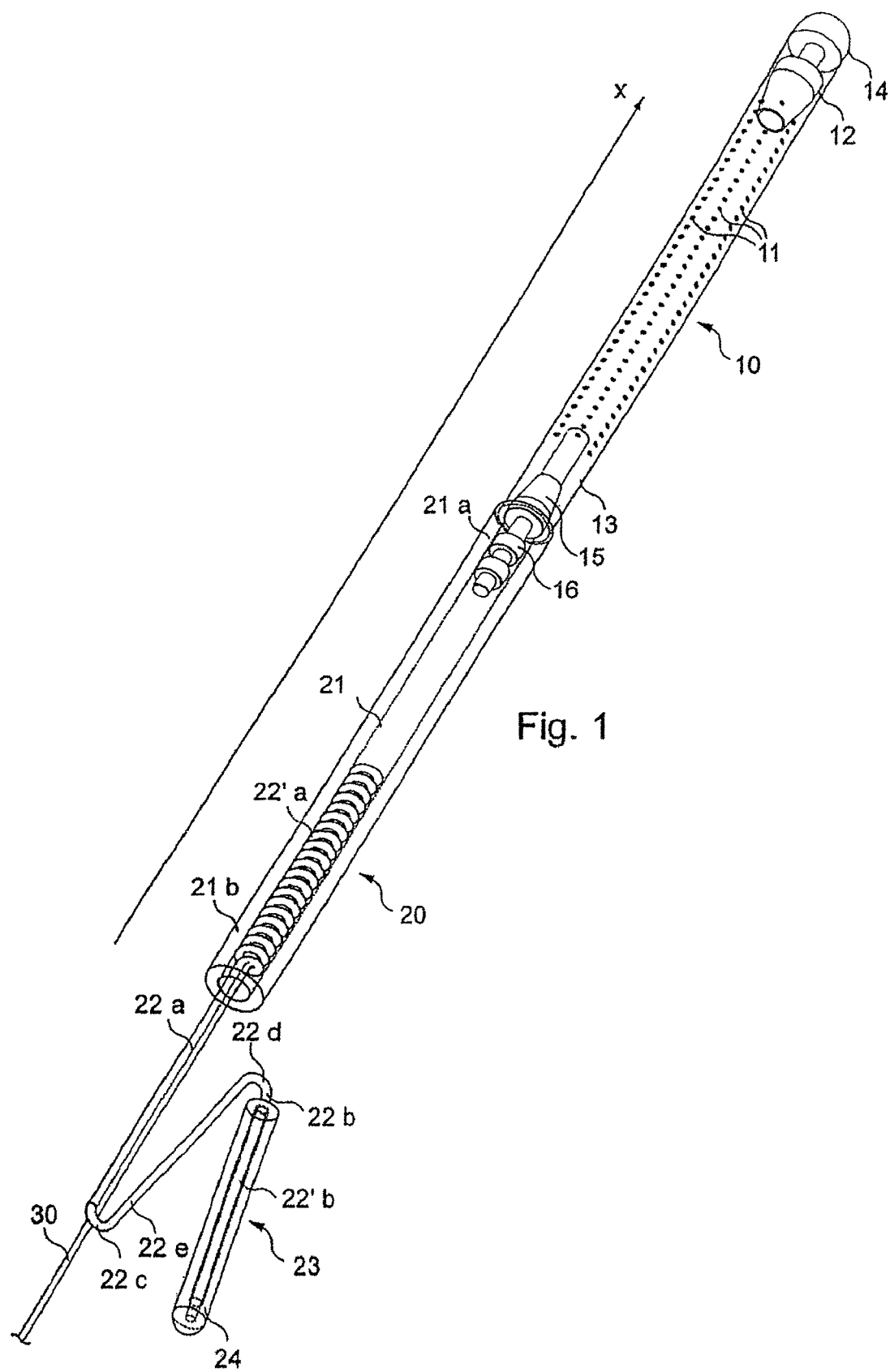
FIG. 1 is a diagrammatic view of a recoverable intrauterine system conforming to one embodiment of the invention.

As shown in FIG. 1, the recoverable intra-uterine system comprises firstly a housing 10 intended to be placed in the uterus.

This housing 10 is intended to be placed in the uterine cavity for a period between a few hours and a few days with a view to pre-implantation development of an embryo in vivo.

To this end, the housing 10 is adapted to contain an embryo, male and/or female gametes, a fertilized ovocyte, an unfertilized ovum or a combination of these various elements.

This housing 10 can be produced in silicone and provided with a series of perforations 11 in its wall enabling interaction between the interior of the housing and the exterior medium in which the housing 10 is placed, that is to say the uterine medium.

As clearly shown in FIG. 1, this housing 10 is of elongate shape along an axis X.

In this embodiment, the housing 10 consists of an elongate cylindrical tube.

By way of nonlimiting example, the length of the housing in the direction X can be substantially equal to 10 mm, the inside diameter of the housing 10 being between 0.4 and 0.5 mm and the outside diameter of the cylindrical housing 10 being between 0.7 and 0.8 mm.

This elongate housing 10 therefore has, in the direction of its introduction into a uterine cavity along the axis X, a distal end 12 and a proximal end 13.

The housing 10 has at its distal end 12 a stopper 14, for example of titanium, which is a tight fit in the end of the housing 10 and closes it. This stopper 14 can be removed after use of the intra-uterine system to extract the embryos and/or elements that have been placed temporarily in the uterine cavity, in particular with a view to their selection and re-implantation in the uterine cavity.

The housing 10 also has a proximal stopper 15 at its proximal end 13.

The housing 10 is associated with a device 20 for retaining the intrauterine system in the uterus. This retaining device 20 is disposed at the proximal end 13 of the housing 10.

In this embodiment, the retaining device 20 comprises a cylindrical tube 21, a bent wire 22 forming a spring and a retaining arm 23.

The cylindrical tube 21 is fixed at one end 21a to the proximal end 13 of the housing 10.

In practice, the proximal stopper 15 includes an extension 16 the diameter whereof is adapted to fit inside the cylindrical tube 21, at one end 21a.

For example, this extension 16 is glued to the cylindrical tube 21.

The stopper 15 is assembled to the housing 10 at the proximal end 13 simply because the housing 10 is a tight fit over the stopper 15.

In practice, this stopper 15 can have a frustoconical shape enabling a sealed fit of the stopper 15 in the end 13 of the housing 10.

The cylindrical tube 21 is produced in a biocompatible material, like the housing 10, for example silicone.

In practice, this cylindrical tube 21 can have a length of the same order as that of the housing 10, substantially equal to 10 mm, and have a diameter slightly greater than that of the housing 10.

By way of nonlimiting example, the inside diameter of the cylindrical tube 21 can be between 0.5 and 0.6 mm and the outside diameter of the cylindrical tube 21 can be between 0.9 and 1 mm.

The cylindrical tube 21 is therefore aligned with the housing 10 in the direction of the axis X.

The bent wire 22 forming a spring is mounted in the cylindrical tube 20 at its second end 21b.

In practice, the bent wire 22 forming a spring is attached to the inside of the cylindrical tube 21.

In practice, in this embodiment, the bent wire 22 forming a spring has a first end 22a disposed in the cylindrical tube 21, at the proximal end 13 of the housing 10, and a second end 22b.

The first end 22a of the bent wire 22 forming the spring extends in the direction of the axis X in alignment with the housing 10 and the cylindrical tube 20.

The terminal portion 22'a of the first end 22a is conformed as a coil spring. This coil spring portion is attached to the inside of the cylindrical tube 20, for example by means of a silicone adhesive.

The second end 22b of the bent wire 22 forming a spring comprises a terminal portion covered by a protective sleeve 24. This terminal portion of the second end 22b covered by the protective sleeve 24 constitutes the retaining arm 23 of the retaining device, this retaining arm being adapted to retain the device in the uterine cavity as described hereinafter.

In this particular embodiment, the bent wire 22 forming a spring includes two bends 22c, 22d so that an intermediate portion 22e extends between the first end 22a and the second end 22b of the bent wire 22 forming a spring.

In practice, this bent wire 22 forming a spring can be produced from a stainless steel spring of which a first part, corresponding to the terminal portion 22'a of the first end 22a, is conformed as a coil spring and a second part is straightened and bent to produce a rectilinear portion of the first end 22a, the intermediate portion 22a and the second end 22b of the bent wire.

Thus the retaining arm 23 produced at the second end 22b of the bent wire 22 forming a spring is arranged on elastic means consisting mainly of the intermediate part 22e and the bends 22c and 22d of the bent wire 22 forming a spring.

As shown clearly in FIG. 1, these elastic means exert a force returning. the retaining arm 23 to a stable position in which the retaining arm 23 is moved away from the axis X along which the housing 10, the cylindrical tube 20 and the first end 22a of the bent wire forming a spring extend.

By way of nonlimiting example, the diameter of the steel wire used to form the bent wire forming a spring can be between 0.1 and 0.2 mm.

The length of the coil spring portion 22'a can be substantially equal to half the length of the cylindrical tube 20, and for example equal to 5 mm.

Moreover, the protective sleeve 24 can be produced from a nylon tube mounted on the terminal portion 22'b of the second end 22b of the bent wire 22. This nylon tube can be glued to the steel wire, for example using a silicone glue.

By way of nonlimiting example, the length of the protective sleeve can be substantially equal to 5 mm, the outside diameter being between 0.4 and 0.5 mm and the inside diameter being between 0.15 and 0.25 mm to enable introduction of the steel wire.

In addition to this retaining device 20 fixed to the housing 10, the recoverable intra-uterine system also includes a removal thread 30 for pulling the device out of the uterus.

This removal thread 30 can be of nylon and have a total length of 150 mm and a diameter of 0.1 mm.

In this embodiment, this nylon thread 30 is fastened to the terminal portion 22'a in the form of a coil spring.

In practice, the nylon thread 20 can be fixed to the interior of the spiral of the coil spring, before the spiral is introduced into the cylindrical tube 21. By heating this terminal portion 22'a, the nylon thread is welded to the inside of the spiral and thus fastened to the bent wire 22.

The terminal portion 22'a associated with the removal thread 30 is then introduced into the cylindrical tube 21 and glued as indicated above by means of a silicone glue.

The various positions that the retaining arm 23 can assume when using the recoverable intra-uterine system are described next with reference to FIGS. 2 to 5.

In practice, the housing 10 is assembled to the retaining device, and more particularly to the cylindrical tube 21, after introducing into the housing elements such as male and female gametes.

During the introduction of these elements, the distal stopper 14 is in place at the distal end 12 of the housing 10.

After introducing the gametes, the stopper 15 is fitted to the end 13 of the housing 10, at the same time as fitting the retaining device 20 because the cylindrical tube 21 is fixed to the extension 16 of the proximal stopper 15.

Figure 2:
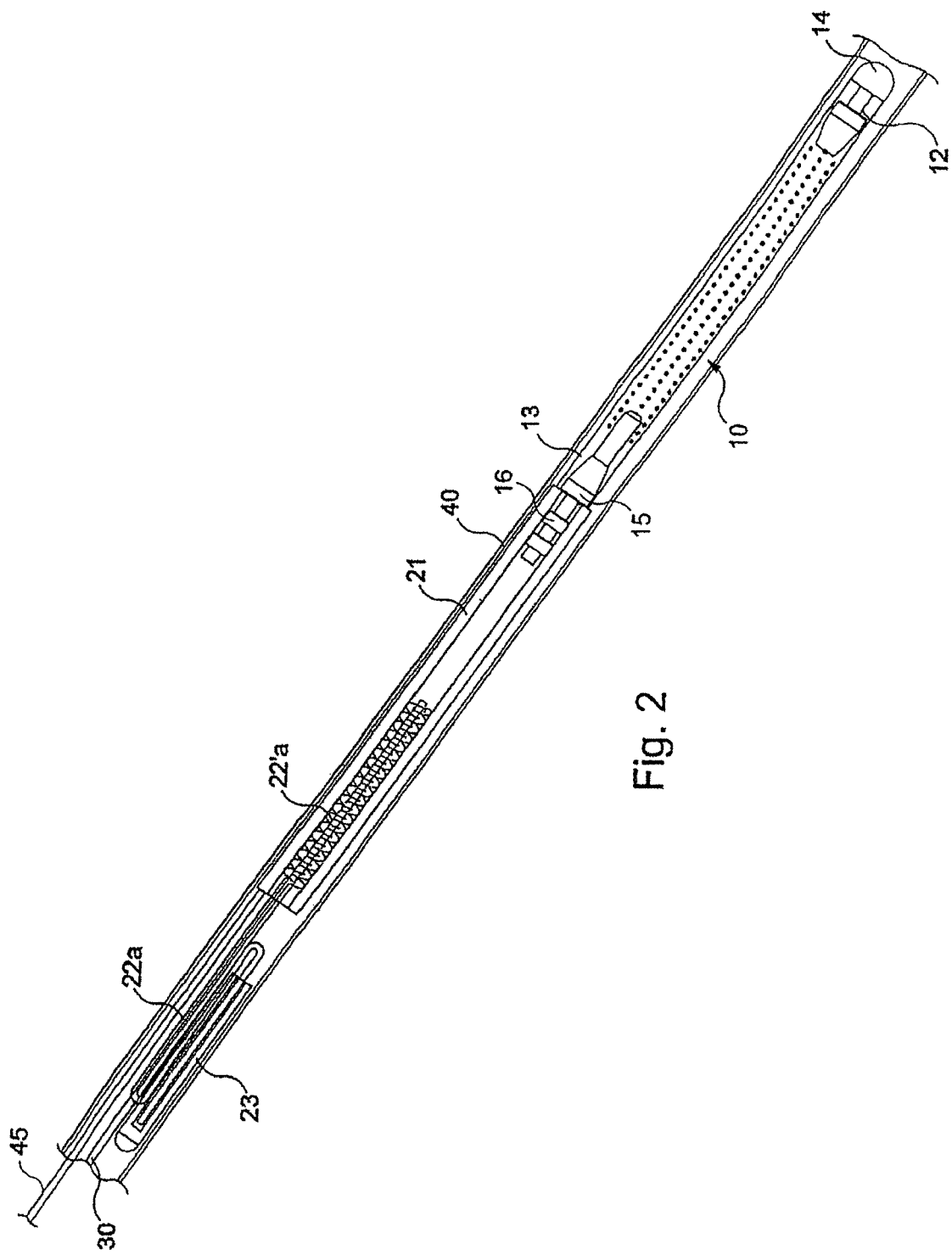
FIG. 2 is a perspective view diagrammatically illustrating the fitting of a recoverable intra-uterine system from FIG. 1 into a transfer catheter.

For the introduction of the intra-uterine system into the uterine cavity there is used, in the conventional way, as shown in FIG. 2, a catheter 40 that takes the overall form of an elongate cylindrical tube of appropriate length able to accommodate the whole of the intra-uterine system, that is to say, successively, the housing 10, the cylindrical tube 20 and the wire 22 forming a spring associated with the retaining arm 23.

Moreover, the removal thread 30 extends beyond the transfer catheter.

Furthermore, a semi-rigid rod 45 is also used, bearing on the retaining device, at the free end 21b of the cylindrical tube 21.

Figure 3:
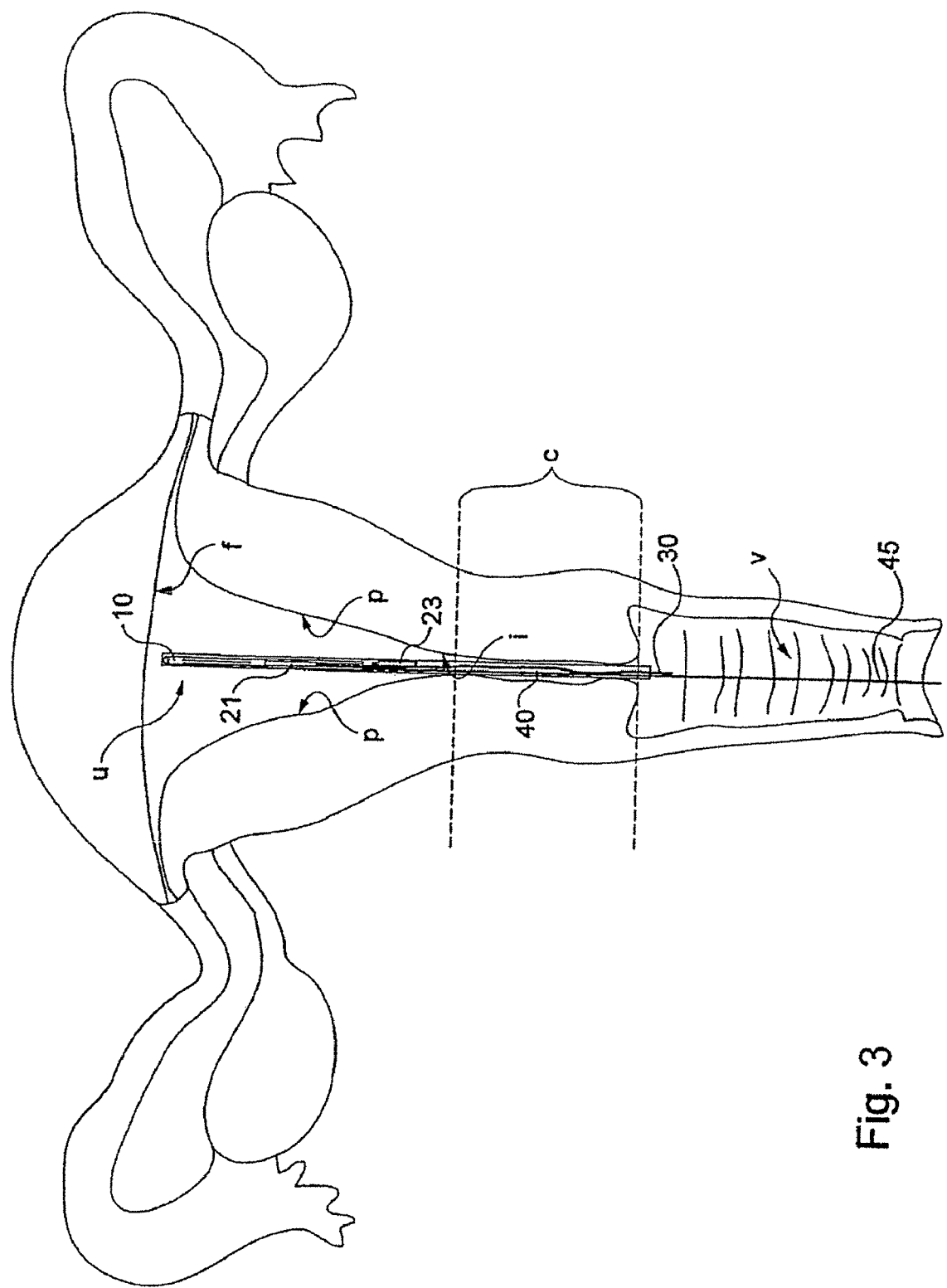
FIG. 3 is a view in section illustrating diagrammatically the recoverable intra-uterine system from FIG. 1 during its introduction into the uterine cavity.

As clearly shown in FIG. 3, this semi-rigid rod is sufficiently long to project from the free end of the catheter.

In this introduction position, as clearly shown in FIG. 2, the retaining arm 23 is substantially parallel to the axis X of the housing 10 and is an extension of the housing 10.

In practice, in this introduction position, the bent wire forming a spring is compressed to close up the angles at the bends 22c and 22d against the return force exerted by the wire 22 forming a spring.

In this position, the first and seconds ends 22a, 22b and the intermediate portion 22e are adjacent to each other and in a direction parallel to the axis X.

The retaining arm 23 is then aligned with the cylindrical tube 21 and the housing 10, beyond the free end 21b of the cylindrical tube 21, so as not to constitute an increased thickness and to enable introduction of the whole of the system into the transfer catheter 40.

As clearly shown in FIG. 3, the system in its introduction position is introduced into the uterine cavity u until the whole of the system lies beyond the cervix.

To be more precise, the whole of the system inside the transfer catheter 40 passes successively through the vagina v, then the cervix c before entering the uterine cavity.

Figure 4:
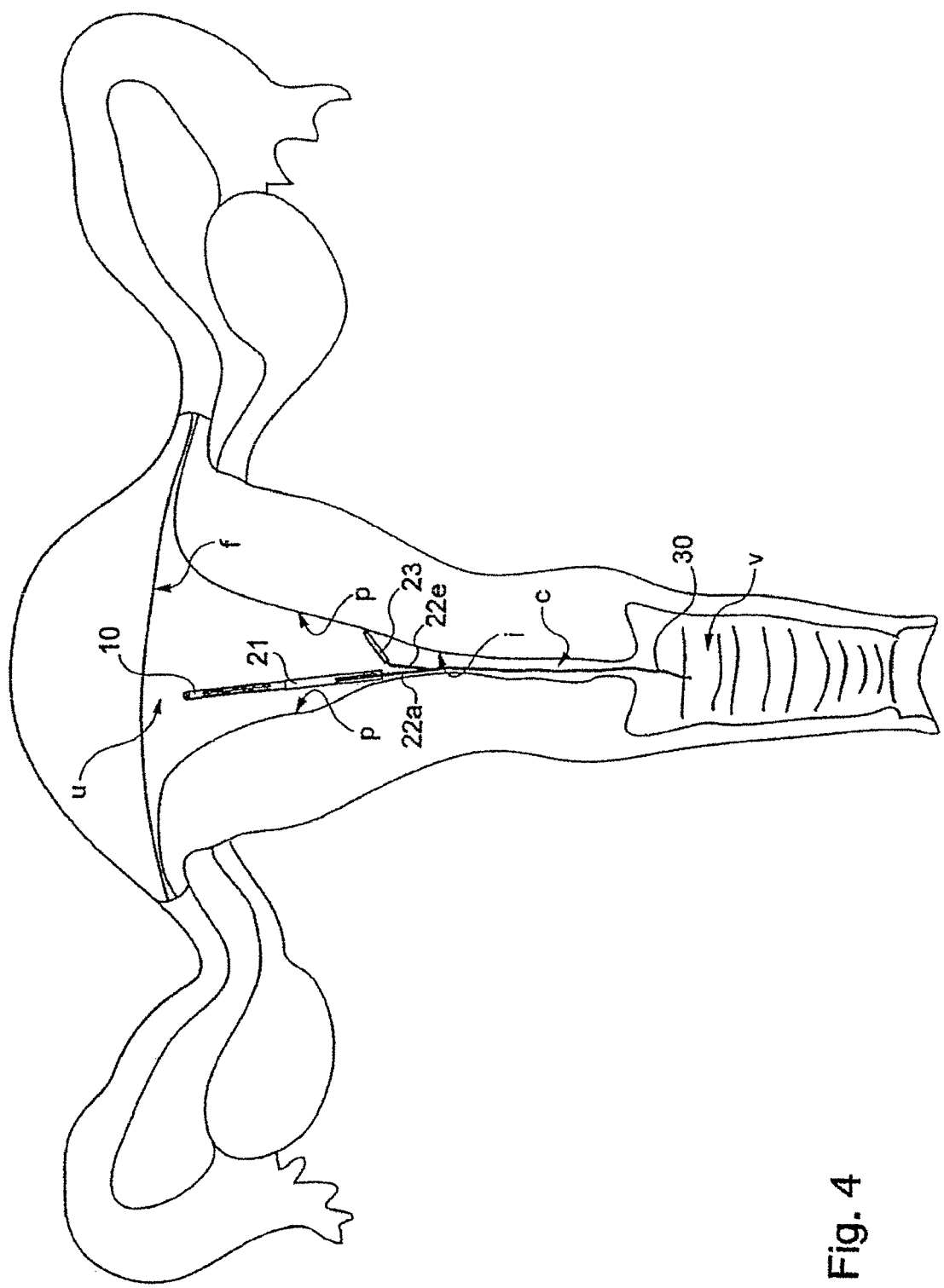
FIG. 4 is a figure analogous to FIG. 3 illustrating the recoverable intra-uterine system in the uterine cavity.

After removal of the catheter, as shown in FIG. 4, the elastic means of the wire 22 forming a spring are adapted to position the retaining arm 23 in a position away from the axis X of the housing, corresponding to a free position of retention in the uterine cavity.

To remove the catheter, the practitioner holds the housing 10 associated with the retaining device 20 in position using the semi-rigid rod 45.

Whilst retaining the device in place using the semi-rigid rod, the practitioner withdraws the catheter 40 in translation along the semi-rigid rod 45.

Once the catheter has been entirely withdrawn, the semi-rigid rod 45 is also withdrawn, the housing 10 being retained inside the uterine cavity in particular by the positioning of the retaining arm 23 in a position away from the axis X of the housing 10.

As shown clearly in FIG. 4, the contact of the retaining arm 23 inside the uterine cavity is limited to the portion close to the cervix c, in the vicinity of the cervical channel i.

Then, on removal of the device after a period of pre-implant development, as shown in FIG. 3, the retaining arm 23 is adapted to assume a removal position in which it is substantially parallel to the axis X of the housing.

In practice, in this removal position, the retaining arm 23 pivots about a bend 22d connecting the second end 22b to the intermediate portion 22e of the bent wire 22 forming a spring.

This removal position of the retaining arm 23 substantially parallel to the axis X is thus the opposite of the introduction position.

Figure 5:
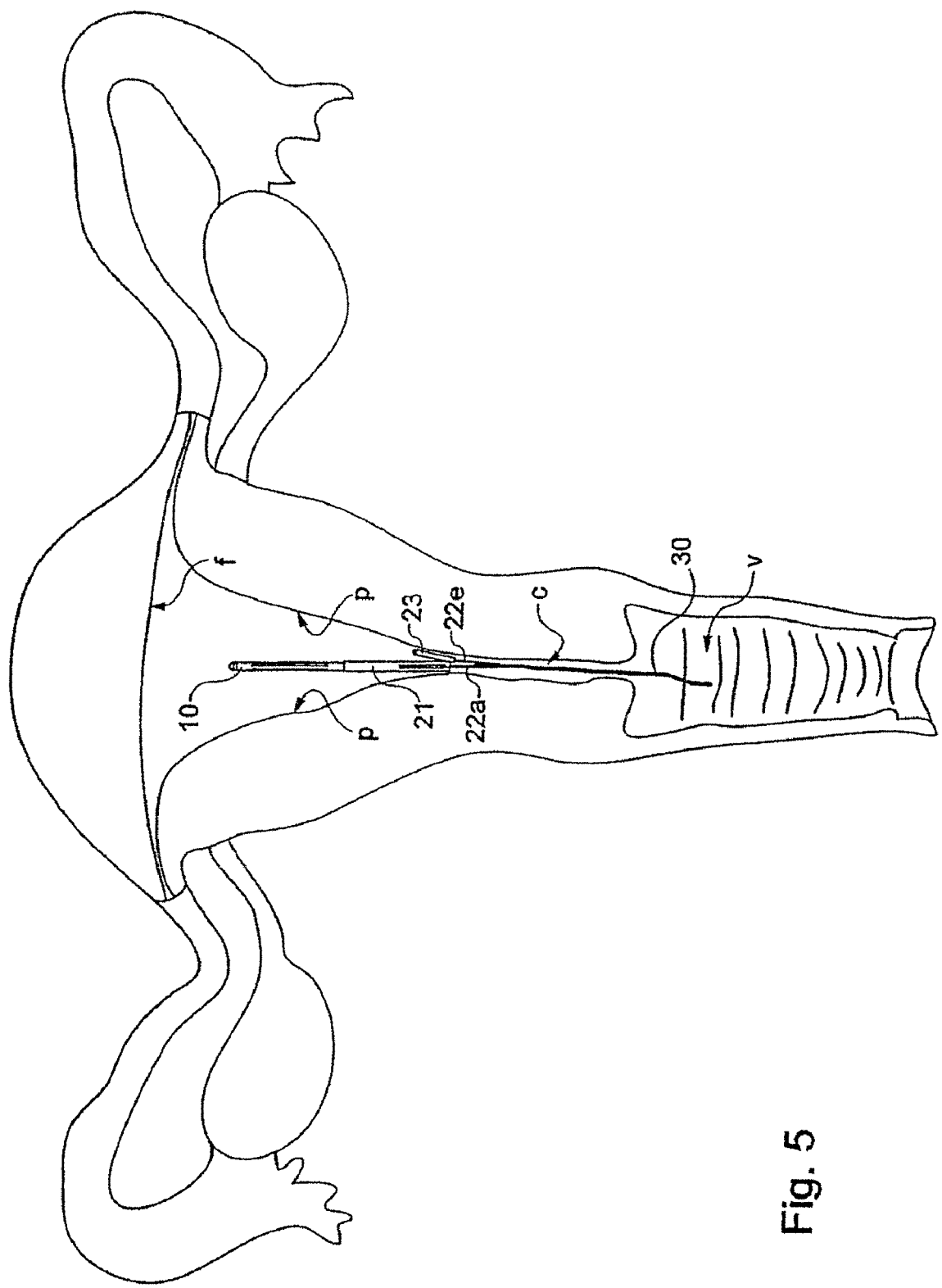
FIG. 5 is a view analogous to FIGS. 3 and 4 illustrating the recoverable intra-uterine system during its removal from the uterine cavity.

As clearly shown in FIG. 5, on removal of the device, the retaining arm 23 comes into contact with only a very small portion of the endometrium, in the vicinity of the cervical channel i.

Thus thanks to mounting the retaining arm 23 on the bent wire 22 forming a spring, this retaining arm 23 can assume two distinct and opposed positions for introduction and removal of the system, providing optimum limitation of the contact between the retaining arm and the endometrium during movements of the system.

Thus the endometrial layer that covers the uterine cavity in its fundus portion f, the body portion p and the cervical channel portion i comes very little into contact with the device introduced into the uterine cavity u, and in particular the retaining device.

The latter comes mainly into contact with the cervix c, which has no endometrial layer, and to a lesser degree with the cervical channel i.

This feature is particularly important when, at the time of implanting the embryo, the latter is placed in contact with the endometrial layer of the uterus to enable nidation and development of the embryo in the uterus.

Of course, the present invention is not limited to the embodiment described above.

In particular, the retaining device could include a number of retaining arms, for example disposed symmetrically relative to the longitudinal axis X of the housing 10.

Moreover, how the retaining arm is mounted at the proximal end 13 of the housing 10 is not limiting on the invention in any way.

Thus the cylindrical tube 21 could be dispensed with, the wire 22 forming a spring being fixed directly at its end 22a to the proximal end 13 of the housing 10.

Moreover, the wire 22 forming a spring could include only one bend 22c, with no intermediate portion 22e, the bend 22c connecting the first portion 22a directly to the second portion 22b.

The retaining arm 23 would then be adapted to occupy only two positions, a free retaining position in which the retaining arm is moved away from the axis X of the housing 10, and an introduction and removal position in which the retaining arm is disposed substantially parallel to the axis X of the housing 10, aligned with that housing 10 and the cylindrical tube 21.

The invention claimed is:

1. A recoverable intra-uterine device comprising:
   a housing adapted to contain at least one element comprising an embryo, male gametes, female gametes, a fertilized ovocyte, an unfertilized ovum, or a combination thereof,
      said housing having along an axis (X) a distal end and a proximal end, and
   a retaining device for retaining the recoverable intra-uterine device in a uterus,
      wherein said retaining device is arranged at the proximal end of the housing and includes at least one retaining arm adapted to assume at least two positions in the uterine cavity of said uterus, said positions comprising:
         a free position,
            wherein the at least one retaining arm is away from the axis (X); and
         a removal position,
            wherein said at least one retaining arm is substantially parallel to said axis (X), and
      further wherein:
         said retaining device comprises at least one bent wire forming a spring having a first end at said proximal end of the housing and a second end fastened to said retaining arm; and
         a terminal portion of said first end of the bent wire forming a spring comprises a coil spring and is fastened in a cylindrical tube of biocompatible material fixed to said proximal end of said housing.

2. The recoverable intra-uterine device of claim 1, wherein said retaining arm comprises a terminal portion of said second end of the bent wire forming a spring, said terminal portion being covered by a protective sleeve.

3. The recoverable intra-uterine device of claim 2, wherein said bent wire forming a spring comprises two bends, said retaining arm being adapted to assume the removal position opposite the introduction position by pivoting about one of said bends of the bent wire forming a spring.

4. A system comprising a transfer catheter and the recoverable intra-uterine device of claim 2, wherein said recoverable intra-uterine device is housed in said catheter.

5. The recoverable intra-uterine device of claim 1, wherein said at least one retaining arm is further adapted to assume at least one introduction position wherein said at least one retaining arm is substantially parallel to said axis (X) of the housing and is an extension of said housing.

6. A system comprising a transfer catheter and the recoverable intra-uterine device of claim 5, wherein said recoverable intra-uterine device is housed in said catheter.

7. The recoverable intra-uterine device of claim 1, wherein said bent wire forming a spring comprises two bends, said retaining arm being adapted to assume the removal position opposite the introduction position by pivoting about one of said bends of the bent wire forming a spring.

8. A system comprising a transfer catheter and the recoverable intra-uterine device of claim 7, wherein said recoverable intra-uterine device is housed in said catheter.

9. The recoverable intra-uterine device of claim 1, further comprising a thread for removing said device fixed by insertion in said coil spring.

10. A system comprising a transfer catheter and the recoverable intra-uterine device of claim 1, wherein said recoverable intra-uterine device is housed in said catheter.

* * * * *